US008683872B1

(12) United States Patent
Khachaturian et al.

(10) Patent No.: US 8,683,872 B1
(45) Date of Patent: Apr. 1, 2014

(54) TEST WEIGHT

(76) Inventors: Jon E. Khachaturian, Houston, TX (US); Matthew T. Khachaturian, Houston, TX (US)

(*) Notice: Subject to any disclaimer, the term of this patent is extended or adjusted under 35 U.S.C. 154(b) by 324 days.

(21) Appl. No.: 13/296,961

(22) Filed: Nov. 15, 2011

Related U.S. Application Data

(60) Provisional application No. 61/414,723, filed on Nov. 17, 2010.

(51) Int. Cl.
*G01N 3/00* (2006.01)
(52) U.S. Cl.
USPC ............................................. 73/788; 177/50
(58) Field of Classification Search
USPC ................................ 73/760, 788, 731; 177/50
See application file for complete search history.

(56) References Cited

U.S. PATENT DOCUMENTS

| | | | | |
|---|---|---|---|---|
| 4,538,849 A * | 9/1985 | Khachaturian et al. | ...... | 294/81.1 |
| 5,662,311 A * | 9/1997 | Waedekin et al. | ............ | 254/273 |
| 6,639,959 B1 * | 10/2003 | Capobianco et al. | ......... | 376/248 |
| 7,155,987 B1 * | 1/2007 | Tumlin | .................... | 73/862.393 |
| 7,814,921 B1 * | 10/2010 | Ranieri et al. | ................ | 135/123 |
| 8,079,791 B2 * | 12/2011 | Ness | ............................... | 410/31 |
| 8,201,440 B2 * | 6/2012 | Brougher | ......................... | 73/81 |

* cited by examiner

*Primary Examiner* — Max Noori
(74) *Attorney, Agent, or Firm* — Garvey, Smith, Nehrbass & North, L.L.C.; Charles C. Garvey, Jr.; Vanessa M. D'Souza

(57) ABSTRACT

A test weight providing an elongated flanged beam having a web, an upper flange connected to the web and a lower flange connected to the web. A pair of openings in the upper flange are provided on the opposing sides of the web. Plurality of plates are connected to the beam, each plate resting upon the lower flange and extending upwardly towards the upper flange. A pair of padeye lift plates are provided, one on each side of the web, each padeye plate having a portion that extends above the upper flange and through an upper flange opening. The test weights are stackable one a upon the other, wherein each of the padeye plates can be pinned to the flanged beam.

30 Claims, 5 Drawing Sheets

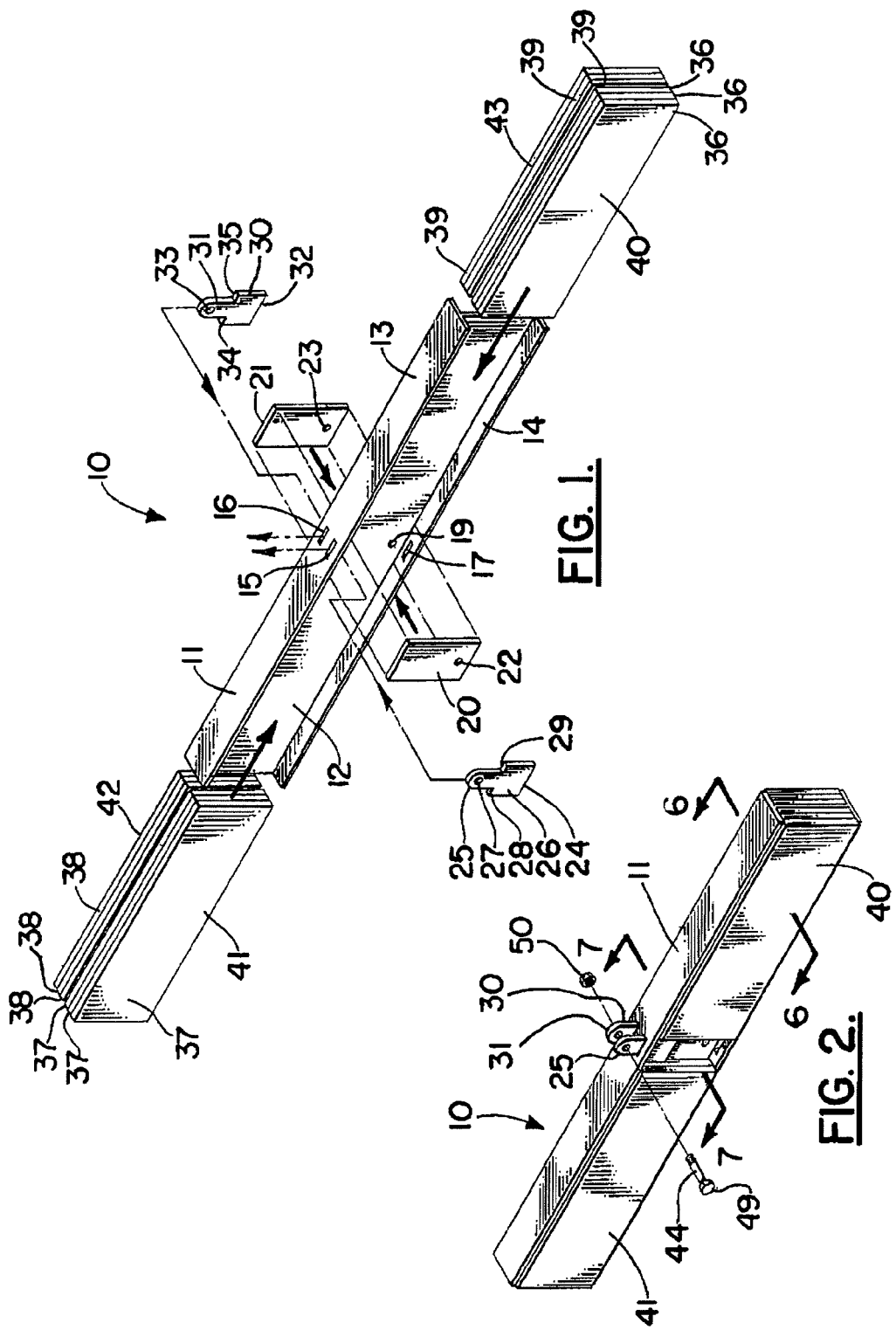

TEST WEIGHT

CROSS-REFERENCE TO RELATED APPLICATIONS

This is a non provisional patent application of U.S. Provisional Patent Application Ser. No. 61/414,723, filed 17 Nov. 2010.

Priority of U.S. Provisional Patent Application Ser. No. 61/414,723, filed 17 Nov. 2010, hereby incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to weights for testing lifting devices and rigging that is used by lifting devices. More particularly the present invention relates to an improved test weight that is constructed using a flanged beam having a lower flange that supports multiple weights and wherein a specially configured pad eye arrangement enables one weight to be stacked upon another and wherein a pad eye forms a connection with another test weight or can be use to connect a lifting device "crane, sling, shackle, pin" for lifting the test weight.

2. General Background of the Invention

Machines and devices that are employed for lifting heavy objects must be tested to a certain percentage over their rated load capacity. Thus, it is important to test the load capacity of lifting devices such as cranes, winches, wire rope, lifting lines, slings, lifting bars and the like. As used herein, the term "rigging" is to be construed in the broadest possible sense to include any device that can be used to lift a heavy object. A lifting device as used herein should be considered in its broadest sense to cover any device that is employed to lift a heavy object such as for example cranes, winches, fork lifts, lifting booms, and the like.

In order to test the weight of any lifting device or any item of rigging, a test weight should be constructed that is easy to attach to the selected item to be rated. It is also desirable to combine multiple weights together in order to attain the required load for a specific test.

BRIEF SUMMARY OF THE INVENTION

A test weight includes an elongated flanged beam having a web, an upper flanged connected to the web and a lower flange connected to the web. A pair of openings are provided in the upper flange, the openings being on opposing sides of the web;

A plurality of plates are connected to the beam, each plate resting upon the lower flange and extending upwardly to the upper flange.

A pair of padeye lift plates are attached, one on each side of the web. Each padeye plate has a portion that extends above the upper flange and through an upper flange opening.

In one embodiment, the beam can be an I-beam. In one embodiment, the test weight can employ a wide flange beam.

In one embodiment, there are a plurality of plates on each side of the each padeye plate.

In one embodiment, a web plate stiffener is attached to the web. In one embodiment, there are a pair of web plates. In one embodiment, the plates are on opposed sides of the web.

In one embodiment, openings in the padeye plates enable connection of a pin to the padeye plates at the openings.

In one embodiment, there are upper and lower openings in the padeye plates.

The apparatus of the present invention includes a test weight, comprising an elongated flanged beam having beam end portions, a web, an upper flange connected to the web and a lower flange connected to the web, a pair of opening in the upper flange, the openings being on opposing sides of the web, a plurality of plates connected to the beam, each plate resting upon the lower flange and extending upwardly to the upper flange, a pair of padeye lift plates, one on each side of the web, each padeye plate having a portion that extends above the upper flange and through an upper flange opening, and each plate extending between a beam end portion and a padeye plate, each beam terminating at a padeye plate.

Optionally, the beam is an I-beam.

Optionally, the beam is a wide flange beam.

Preferably, there are a plurality of plates on each side of the each padeye plate.

Preferably, the invention further compromises a web plate stiffener or doubler attached to the web.

Preferably, there are a pair of web plates.

Preferably, the plates are on opposed sides of the web.

Preferably, the invention further compromises openings in the padeye plates that enable connection of a pin to the padeye plates at the openings.

Preferably, the invention further compromises upper and lower openings in the padeye plates.

Preferably, each of the plates has a length that is less than half the length of the beam.

The apparatus of the present invention includes a test weight, comprising a flanged beam having a generally vertically extending web and at least one generally horizontally extending flange connected to the web, one or more weighted plates attached to the flanged beam, each weighted plate resting upon the flange, lifting eyes on the flanged beam, a recess on the bottom of each beam that is receptive of the lifting eyes of another beam when the beams are stacked one upon the other; and an opening in the web that enables one beam to be pinned to another beam when one beam is stacked upon another beam.

Preferably, the invention further compromises a second, and upper flange.

Preferably, the lifting eyes extend above the upper flange.

Optionally, the weighted matter is placed on opposing sides of the web.

Optionally, the weighted matter is resting upon the lower flange.

Optionally, the weighted matter is connected to both a flange and the web.

Preferably, one lifting eye is on one side of the web and the other lifting eye is on the other side of the web for a beam that has another beam stacked upon it.

Preferably, a pin passes through two of the lifting eyes and the web when one beam is stacked upon another beam.

Preferably, there are a pair of beams, one stacked upon the other and wherein a pinned connection joins one to the other.

The apparatus of the present invention includes a test weight, comprising an elongated flanged beam having a web, an upper flange connected to the web and a lower flange connected to the web, a pair of openings in the upper flange, the openings being on opposing sides of the web, a plurality of plates connected to the beam, each plate resting upon the lower flange, and a pair of padeye plates, one on each side of the web, each padeye plate having a portion that extends above the upper flange and through an upper flange opening.

Preferably, there are a pair of beams, one stacked upon the other and wherein a pinned connection joins one to the other.

Preferably, each of the weighted plates has a length that is less than half the length of the beam.

Preferably, the weighted plates are layered one upon the other in face to face engagement.

Preferably, each of the weighted plates terminates at a plate end next to a padeye.

Preferably, the beam has a transverse thickness next to the weighted plates that is greater than the thickness next to the padeyes.

Optionally, each of the plates are metallic.

Optionally, each of the plates are steel.

Preferably, the test weight has a weight of between about five hundred pounds and twenty tons.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is an exploded perspective view of a preferred embodiment of the apparatus of the present invention;

FIG. 2 is a perspective view of a preferred embodiment of the apparatus of the present invention;

DETAILED DESCRIPTION OF THE INVENTION

Figure 3:
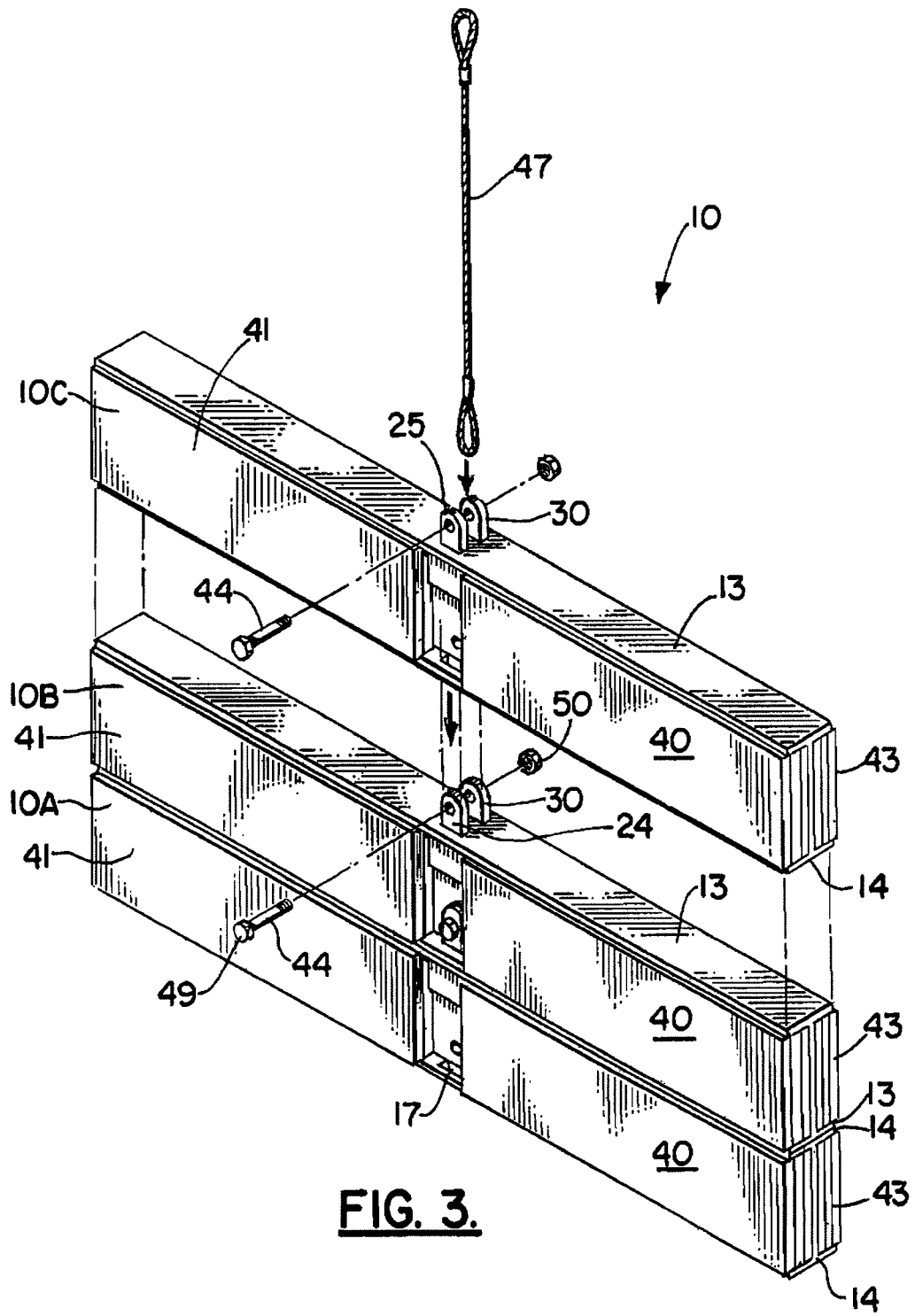
FIG. 3 is another perspective view of a preferred embodiment of the apparatus of the present invention.

FIGS. 1-8 show a preferred embodiment of the apparatus of the present invention designated by the numeral 10. Test weight 10 employs a flanged beam such as an I-beam, channel beam, T beam or wide flanged beam 11. Flanged beam 11 can provide a web 12 and one or more flanges 13, 14. In FIG. 1, the flanges include upper flange 13 and lower flange 14. Flange 13 has a pair of upper openings 15, 16. These openings 15, 16 are on opposing sides of web 12.

A pair of lower openings 17, 18 are provided. Openings 17, 18 are openings in lower flange 14. As with the upper openings 15, 16, the lower openings 17, 18 are on opposing side of web 12. A web opening 19 is provided just above lower flange 14 as shown. A pair of web plate stiffeners 20, 21 are provided for stiffening or strengthening the web 12 next to the openings 15, 16 and 17, 18. In the preferred embodiment, the web plate stiffeners 20, 21 can extend from one upper flange 13 to the other lower flange 14.

Each of the web plate stiffeners 20, 21 provides an opening. The web plate stiffener 20 provides opening 22. The web plate stiffener 21 provides opening 23. Upon assembly of each web plate stiffener 20, 21 to web 12 (e.g. welding), opening 22 and 23 align with web opening 19 (see FIG. 1).

A pair of padeye plates 24, 30 are fixed to web plate stiffeners 20, 21. The padeye plate 24 is attached to web plate stiffener 20. The padeye plate 30 is attached to web plate stiffener 21. The padeye plates 24, 30 each provided an upper section, a lower section, an opening and a pair of shoulders. The padeye plate 24 has upper section 25, lower section 26, opening 27 and shoulders 28, 29 (see FIGS. 1, 6, and 10).

Figure 10:
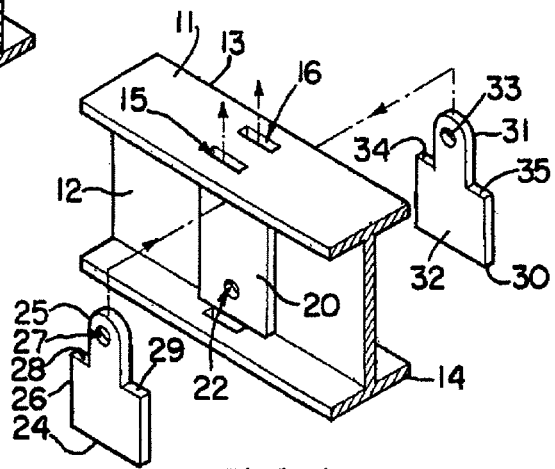
FIG. 10 is a fragmentary perspective view of a preferred embodiment of the apparatus of the present invention.
Figure 11:
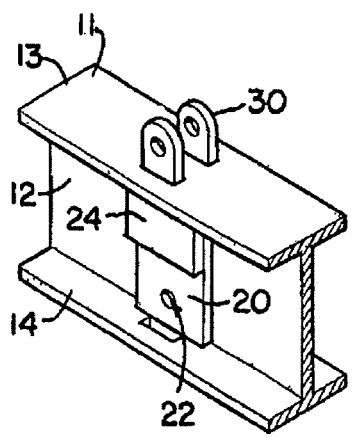
FIG. 11 is a fragmentary perspective view of a preferred embodiment of the apparatus of the present invention.
Figure 12:
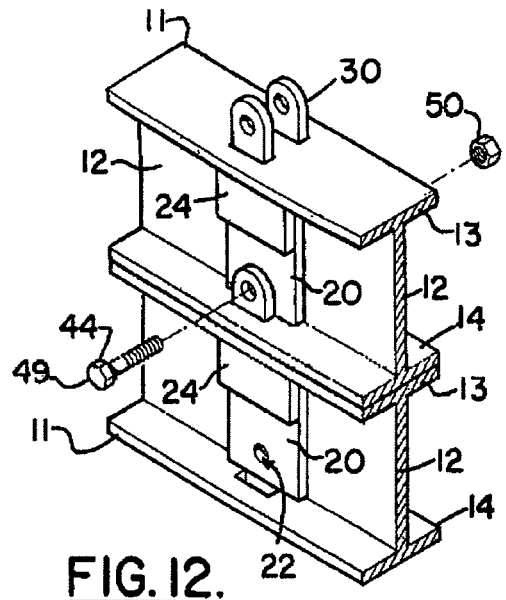
FIG. 12 is a fragmentary perspective view of a preferred embodiment of the apparatus of the present invention.

The padeye plate 30 is similarly configured to plate 24, providing upper section 31, lower section 32, opening 33, and a pair of shoulders 34, 35 (see FIG. 1, 10). The padeye plates 24, 30 attach to beam 11 at openings 15, 16. The padeye plate 24 upper section 25 extends upwardly through upper opening 15 as shown in FIGS. 1, 2, 7 and 9-12. Shoulders 28, 29 engage the lower surface of upper flange 13. Only the upper section 25 of padeye plate 24 extends through and above upper opening 15. Similarly, only the upper section 31 of padeye plate 30 extends through and above upper opening 16 as shown in FIGS. 1, 2, 7 and 9-12.

The web stiffener plates 20, 21 can be welded to web 12. The web stiffener plates 20, 21 can be welded to the upper and lower flanges 13, 14. Padeye plates 24, 30 can be welded to a web stiffener plate 20 or 21. The padeye plates 24, 30 can also be welded to upper flange 13 (see FIG. 1, 7).

A plurality of weights or weighted plates 36-39 are provided in the embodiment shown. Each plurality of three (3) plates 36 or 37 or 38 or 39 forms a bundle. Thus, three of the weights or plates 36 form the bundle 40. Three of the weights or plates 37 form the bundle 41. Three or the weights or plates 38 form the bundle 42. Three of the weight or plates 39 form the bundle 43 (see FIG. 1, 3, 6, 8).

Figures 4, 5:
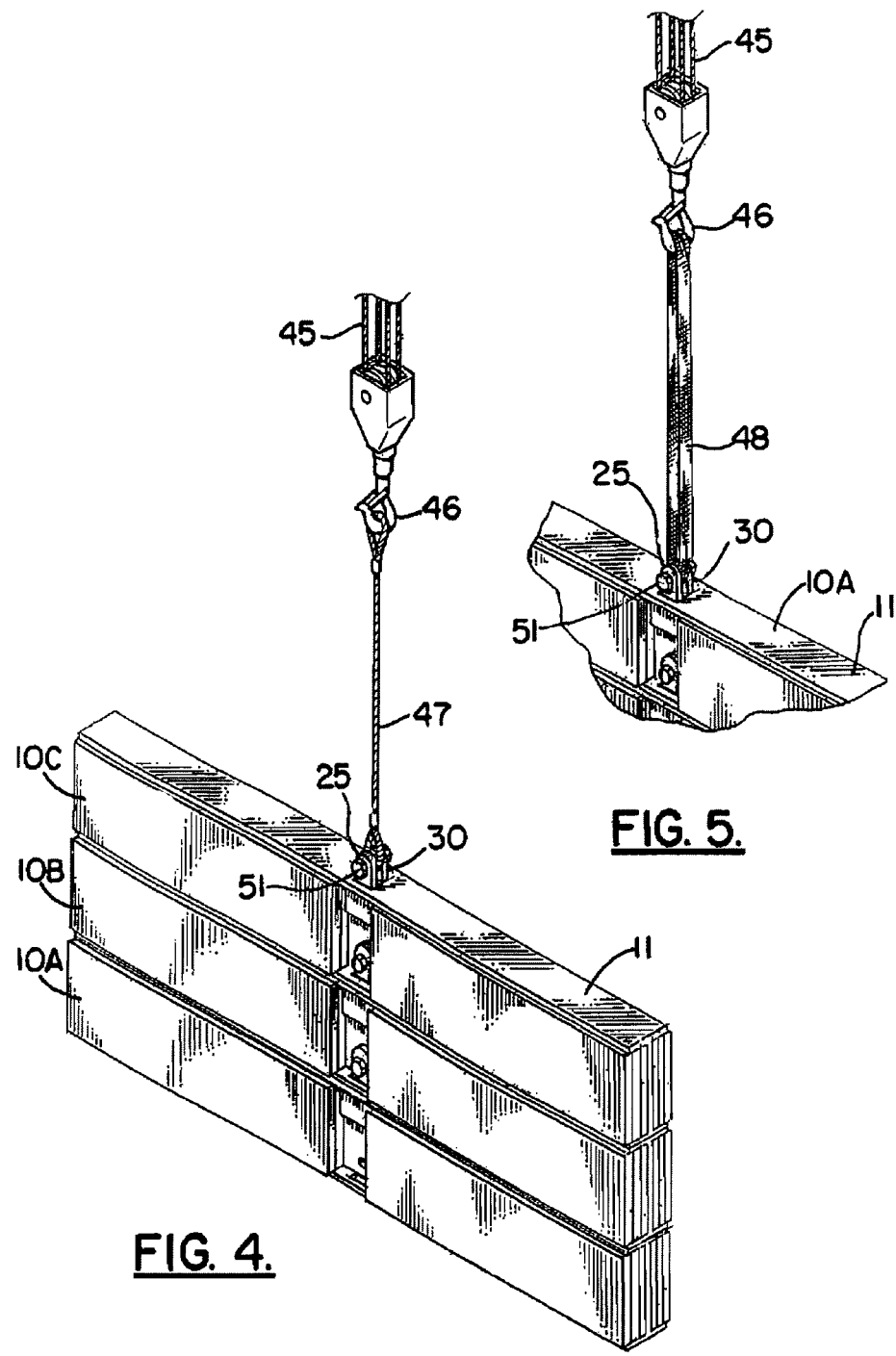
FIG. 4 is a perspective view of a preferred embodiment of the apparatus of the present invention.
FIG. 5 is a partial perspective view of a preferred embodiment of the apparatus of the present invention.
Figure 8:
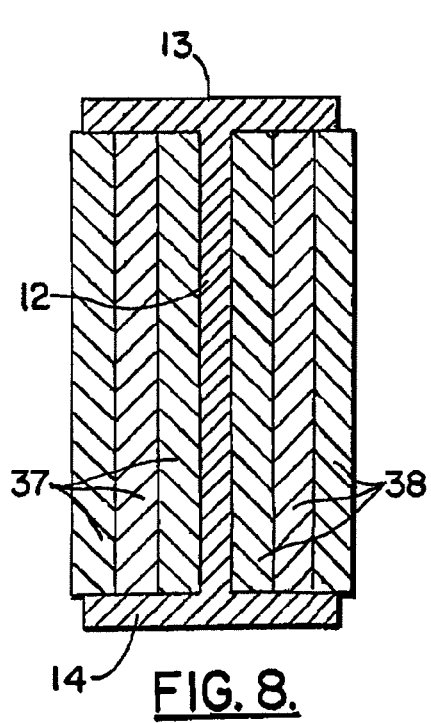
FIG. 8 is a partial, sectional elevation view of a preferred embodiment of the apparatus of the present invention.
Figure 6:
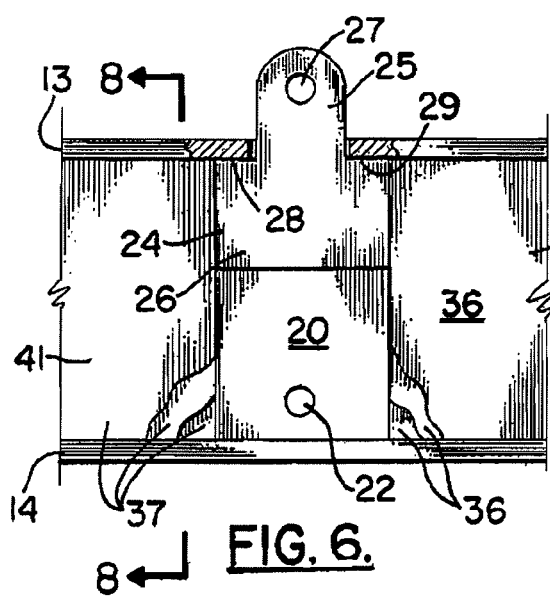
FIG. 6 is a sectional view of a preferred embodiment of the apparatus of the present invention.
Figure 7:
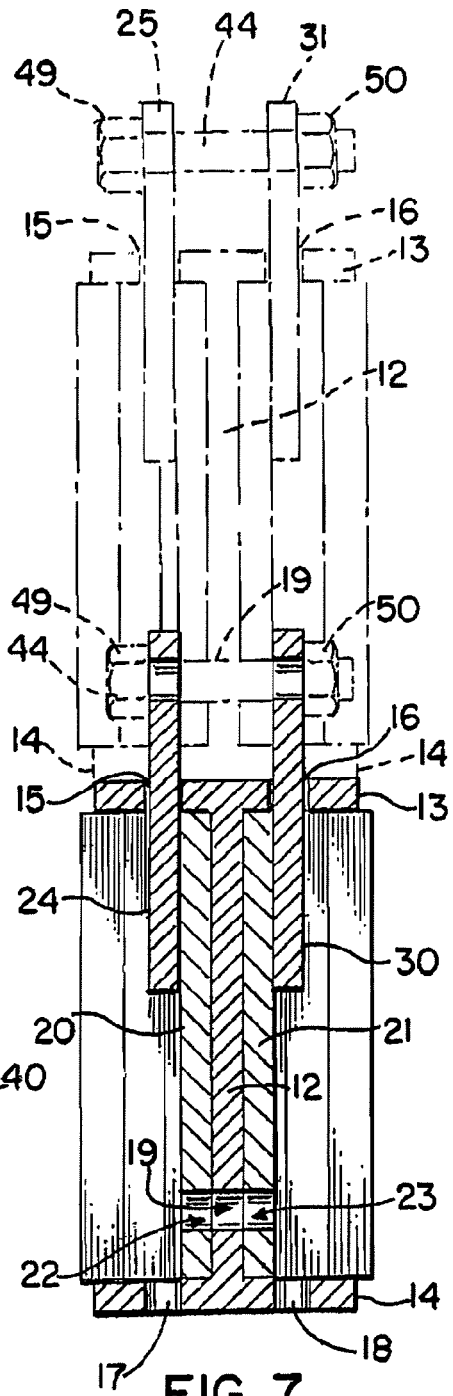
FIG. 7 is a sectional view of a preferred embodiment of the apparatus of the present invention.
Figure 9:
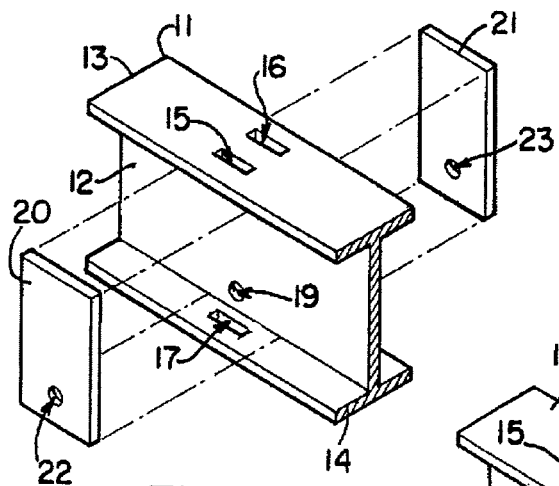
FIG. 9 is a fragmentary perspective view of a preferred embodiment of the apparatus of the present invention.

A pin or pinned connection 44 (e.g. bolt 49 and nut 50) can be used to attach one test weight 10A to another test weight 10B. In FIGS. 3 and 4, three test weights 10A, 10B, 10C are stacked together. In each case, a pin or bolt 49 passes through the openings 27, 33 of the padeye plates 24, 30 respectfully. The pin or bolt 49 also passes through the web opening 19 in web 12 as well as the opening 22 in web plate stiffener 20 and the opening 23 in web plate stiffener 21. Nut 50 connects to bolt 49 (see FIG. 3). This arrangement can be seen in FIGS. 5, 6, 7, 10, 12. Other fasteners or members can be used to form the pin or pinned connection 44 (e.g., a pin, rivet, shaft, or the like).

In FIGS. 4 and 5, a lifting implement such as block, crown block, crane or other lifting device 45 is shown lifting the combination of test weights 10A, 10B, 10C. Rigging such as a sling 47 or a grommet 48 can be used to form a connection with the connected test weights 10A, 10B, 10C and the lifting device 45. As an example, the lifting device 45 can provide a hook 46 that can connect with an eye of a sling 47 or with the loop of a grommet 48. The upper section 25 of a padeye plate 24 and the upper section 31 of a padeye plate 30 can be attached to the sling 47 or the grommet 48 using a pinned or bolted connection 51.

PARTS LIST

The following is a list of parts and materials suitable for use in the present invention:

| Parts Number | Description |
| --- | --- |
| 10 | test weight |
| 10A | test weight |
| 10B | test weight |
| 10C | test weight |
| 11 | flanged beam/I-beam |
| 12 | web |
| 13 | upper flange |
| 14 | lower flange |
| 15 | upper opening |
| 16 | upper opening |
| 17 | lower opening |
| 18 | lower opening |
| 19 | web opening |
| 20 | web plate stiffener |
| 21 | web plate stiffener |
| 22 | opening |
| 23 | opening |
| 24 | padeye plate |
| 25 | upper section |
| 26 | lower section |
| 27 | opening |
| 28 | shoulder |
| 29 | shoulder |
| 30 | padeye plate |
| 31 | upper section |
| 32 | lower section |
| 33 | opening |
| 34 | shoulder |
| 35 | shoulder |
| 36 | weight/plate |
| 37 | weight/plate |
| 38 | weight/plate |
| 39 | weight/plate |
| 40 | bundle |
| 41 | bundle |
| 42 | bundle |
| 43 | bundle |
| 44 | pin/pinned connection |
| 45 | lifting device/implement, block, crown block |
| 46 | hook |
| 47 | sling |
| 48 | grommet |
| 49 | bolt |
| 50 | nut |
| 51 | pinned connection, bolted connection |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A test weight, comprising:
   a) an elongated flanged beam having beam end portions, a web, an upper flange connected to the web and a lower flange connected to the web;
   b) a pair of opening in the upper flange, the openings being on opposing sides of the web;
   c) a plurality of plates connected to the beam, each plate resting upon the lower flange and extending upwardly to the upper flange;
   d) a pair of padeye lift plates, one on each side of the web, each padeye plate having a portion that extends above the upper flange and through an upper flange opening; and
   e) each plate extending between a beam end portion and a padeye plate, each beam terminating at a padeye plate.

2. The test weight of claim 1 wherein the beam is an I-beam.

3. The test weight of claim 1 where in the beam is a wide flange beam.

4. The test weight of claim 1 wherein there are a plurality of plates on each side of the each padeye plate.

5. The test weight of claim 1 further compromising a web plate stiffener or doubler attached to the web.

6. The test weight of the claim 5 wherein there are a pair of web plates.

7. The test weight of claim 6 wherein the plates are on opposed sides of the web.

8. The test weight of claim 1 further comprising openings in the padeye plates that enable connection of a pin to the padeye plates at the openings.

9. The test weight of claim 1 further comprising upper and lower openings in the padeye plates.

10. The apparatus of claim 1 wherein each of the plates has a length that is less than half the length of the beam.

11. A test weight, comprising;
    a) a flanged beam having a generally vertically extending web and at least one generally horizontally extending flange connected to the web;
    b) one or more weighted plates attached to the flanged beam, each weighted plate resting upon the flange;
    c) lifting eyes on the flanged beam;
    d) a recess on the bottom of each beam that is receptive of the lifting eyes of another beam when the beams are stacked one upon the other; and
    e) an opening in the web that enables one beam to be pinned to another beam when one beam is stacked upon another beam.

12. The apparatus of claim 11 further comprising a second, and upper flange.

13. The apparatus of claim 12 wherein the lifting eyes extend above the upper flange.

14. The apparatus of claim 11 wherein the weighted matter is placed on opposing sides of the web.

15. The apparatus of claim 13 wherein the weighted matter is resting upon the lower flange.

16. The apparatus of claim 11 wherein the weighted matter is connected to both a flange and the web.

17. The apparatus of claim 11 wherein one lifting eye is on one side of the web and the other lifting eye is on the other side of the web for a beam that has another beam stacked upon it.

18. The apparatus of claim 11 wherein a pin passes through two of the lifting eyes and the web when one beam is stacked upon another beam.

19. The apparatus of claim 10 wherein there are a pair of beams, one stacked upon the other and wherein a pinned connection joins one to the other.

20. A test weight, comprising:
    a) an elongated flanged beam having a web, an upper flange connected to the web and a lower flange connected to the web;
    b) a pair of openings in the upper flange, the openings being on opposing sides of the web;
    c) a plurality of plates connected to the beam, each plate resting upon the lower flange; and
    d) a pair of padeye plates, one on each side of the web, each padeye plate having a portion that extends above the upper flange and through an upper flange opening.

21. The apparatus of claim 20 wherein there are a pair of beams, one stacked upon the other and wherein a pinned connection joins one to the other.

22. The apparatus of claim 20 wherein each of the weighted plates has a length that is less than half the length of the beam.

23. The apparatus of claim 20 wherein the weighted plates are layered one upon the other in face to face engagement.

24. The apparatus of claim 20 wherein each of the weighted plates terminates at a plate end next to a padeye.

25. The apparatus of claim 20 wherein the beam has a transverse thickness next to the weighted plates that is greater than the thickness next to the padeyes.

26. The apparatus of claim 20 wherein each of the plates are metallic.

27. The apparatus of claim 20 wherein each of the plates are steel.

28. The apparatus of claim 1 wherein the test weight has a weight of between about five hundred pounds and twenty tons.

29. The apparatus of claim 11 wherein the test weight has a weight of between about five hundred pounds and twenty tons.

30. The apparatus of claim 20 wherein the test weight has a weight of between about five hundred pounds and twenty tons.

* * * * *